(12) United States Patent
Nakaoka (10) Patent No.: US 8,535,288 B2
(45) Date of Patent: Sep. 17, 2013

(54) ABSORBENT PRODUCT

(75) Inventor: Kenji Nakaoka, Osaka (JP)

(73) Assignee: Livedo Corporation, Ehime (JP)

( * ) Notice: Subject to any disclaimer, the term of this patent is extended or adjusted under 35 U.S.C. 154(b) by 608 days.

(21) Appl. No.: 12/574,150

(22) Filed: Oct. 6, 2009

(65) Prior Publication Data

US 2010/0100069 A1 Apr. 22, 2010

(30) Foreign Application Priority Data

Oct. 17, 2008 (JP) ............................... P2008-268097

(51) Int. Cl.
*A61F 13/20* (2006.01)

(52) U.S. Cl.
USPC .................................................. 604/385.28

(58) Field of Classification Search
USPC 604/385.28, 385.24, 385.101, 385.25–385.27, 604/385.01
See application file for complete search history.

(56) References Cited

U.S. PATENT DOCUMENTS

| | | | |
|---|---|---|---|
| 6,562,017 B1 * | 5/2003 | Nakaoka et al. | 604/385.28 |
| 8,062,279 B2 * | 11/2011 | Miyamoto | 604/385.27 |
| 2001/0023343 A1 * | 9/2001 | Mizutani et al. | 604/385.28 |
| 2004/0019338 A1 | 1/2004 | Litvay et al. | |
| 2004/0260262 A1 * | 12/2004 | Nishitani et al. | 604/385.04 |
| 2005/0113790 A1 * | 5/2005 | Suzuki et al. | 604/385.28 |
| 2007/0191807 A1 | 8/2007 | Hayashi et al. | |
| 2009/0326505 A1 * | 12/2009 | Sugiyama et al. | 604/385.26 |
| 2010/0241098 A1 * | 9/2010 | Brownlee | 604/367 |
| 2010/0305532 A1 * | 12/2010 | Ashton et al. | 604/365 |

FOREIGN PATENT DOCUMENTS

| | | |
|---|---|---|
| JP | 10-179638 | 7/1998 |
| JP | 2003-180739 | 7/2003 |
| JP | 2005-205038 | 8/2005 |
| JP | 2005-533571 | 11/2005 |
| JP | 2006-141761 | 6/2006 |
| JP | 2006-180990 | 7/2006 |
| JP | 2007-135941 | 6/2007 |
| JP | 2007-143697 | 6/2007 |

OTHER PUBLICATIONS

European Search Report (in English language) issued Jan. 21, 2010 in corresponding European Patent Application No. 09 01 2643.

* cited by examiner

*Primary Examiner* — Lynne Anderson
*Assistant Examiner* — Bradley Philips
(74) *Attorney, Agent, or Firm* — Wenderoth, Lind & Ponack, L.L.P.

(57) ABSTRACT

In an absorbent product (1), each of a pair of side wall parts (34) has two side wall end parts (341) bonded on both end portions of a bonded part (33) and a standing part (342) standing up from the main body part (2) between the two side wall end parts (341). The side wall part (34) is folded outwardly at an inner edge of the bonded part (33) and further folded inwardly. Each side wall end part (341) has a bonded section (3411) and a half standing part (3412) which is continuous from the standing part (342). The half standing part (3412) stands up from the main body part (2) lower than the standing part (342) and fits the vicinity of wearer's crotch in wearing. Thus, it is possible to prevent side leakage from the vicinity of end portions in a longitudinal direction of the absorbent product (1).

18 Claims, 9 Drawing Sheets

ABSORBENT PRODUCT

BACKGROUND OF THE INVENTION

1. Field of the Invention

The present invention relates to an absorbent product for receiving excrement from a wearer.

2. Description of the Background Art

In an absorbent product such as an absorbent pad for light incontinence attached on a disposal diaper and underpants, conventionally, a pair of side wall parts (so-called standing gathers) which stand up toward a wearer are provided on both side portions, thereby preventing leakage of excrement such as urine from the sides of the absorbent product.

Normally, in such an absorbent product, the whole of both end portions in a longitudinal direction of side wall parts (hereinafter, referred to as "side wall end parts") is directly fixed on an upper surface (i.e., a top sheet) of a main body part in the absorbent product, and elastic members disposed between the side wall end parts contract to raise the side wall parts toward a wearer. There is a possibility, however, that the side wall parts are hard to stand up in the vicinity of the side wall end parts, which causes leakage of excrement from the sides of the absorbent product due to the lack of heights of the side wall parts.

Japanese Patent Application Laid-Open No. 2003-180739 (Document 1) discloses a tape-type disposal diaper in which a fastening tape provided on a back side of a main body part is fastened on a stomach side of the main body part to form a waist opening and leg openings, where parts of side wall end parts are not bonded on an upper surface of the main body part. Specifically, inner areas in a width direction of the side wall end parts are not bonded on the upper surface of the main body part, and thereby the heights of side wall parts in the vicinity of the side wall end parts are made greater to prevent leakage from the side wall parts. Japanese Patent Application Laid-Open No. 2006-141761 (Document 2) discloses a disposal diaper where inner areas of side wall end parts are not bonded to the main body part, similarly to Document 1. In the disposal diaper of Document 2, elastic members disposed on side wall parts are provided up to areas where the inner areas and the main body part are not bonded.

In the disposal diaper of Document 1, elastic members are disposed between the two side wall end parts while the elastic members are not disposed in the inner areas of the side wall end parts (i.e., the portions which are not bonded on the upper surface of the main body part). Since the side wall end parts do not contract and the level of standing up the side wall parts in the vicinity of the side wall end parts is not sufficient, there is a possibility that moisture such as urine which has reached the side wall end parts will leak from the sides beyond the side wall parts (so-called side leakage occurs). In the disposal diaper of Document 2, since the side wall end parts are directly bonded on the upper surface of the main body part, it is impaired that the side wall parts in the vicinity of the side wall end parts stand up significantly in a direction away from the main body part, to cause side leakage of urine or the like which has reached the side wall end parts.

SUMMARY OF THE INVENTION

The present invention is intended for an absorbent product for receiving excrement from a wearer. It is an object of the present invention to prevent side leakage from the vicinity of end portions in a longitudinal direction of the absorbent product.

The absorbent product comprises: a sheet-like main body part where an absorbent core is positioned between a back sheet and a top sheet; and a pair of side sheets located on both side portions of the main body part, extending in a longitudinal direction of the main body part, and in the absorbent product, each of the pair of side sheets comprises: a strip-like bonded part bonded on the main body part, being one side of a fold line of a side sheet, said fold line being provided over the entire length of the side sheet and an inner edge of the strip-like bonded part being the fold line; and a side wall part which is the other side of the fold line, being folded outwardly at the fold line and further folded inwardly at a position apart from the fold line, and a part of the side wall part standing up from the main body part, the side wall part comprises: two side wall end parts which are bonded on both end portions of the strip-like bonded part; a standing part being continuous from the two side wall end parts between the two side wall end parts and standing up from the fold line; and elastic members arranged over almost entire length in the longitudinal direction of the standing part, contracting the standing part to form gathers, and one side wall end part out of the two side wall end parts comprises: a half standing part being continuous from the standing part and not being bonded to the bonded part nor the main body part, the elastic members being arranged on the half standing part, the half standing part standing up from the main body part by contraction of the elastic members lower than the standing part; and a bonded section which is provided adjacent to the outside of the half standing part and is bonded on the bonded part. With this structure, it is possible to prevent side leakage from the vicinity of end portions in the longitudinal direction of the absorbent product.

According to a preferred embodiment of the present invention, the half standing part is continuous from the standing part to an end of the side sheet. It is thereby possible to sufficiently secure the length of the half standing part and thereby to prevent side leakage from the vicinity of end portions in the longitudinal direction of the absorbent product surely.

According to another preferred embodiment of the present invention, the half standing part is overlaid with an end in the longitudinal direction of the absorbent core. It is thereby possible to absorb moisture which has flown back to the main body part from the side wall parts rapidly.

According to still another preferred embodiment of the present invention, a width of the half standing part gradually decreases as being away from the standing part. Thus, moisture which has reached the side wall end part can be flown back to the main body part quickly.

According to still another preferred embodiment of the present invention, the one side wall end part further comprises a tubular space forming part which is continuous from the standing part and located adjacent to the outside of the bonded section and folded tubularly, to form a tubular space extending in the longitudinal direction. With this structure, moisture which has reached the side wall end part can be temporally retained, and it is thereby possible to prevent side leakage from the vicinity of end portions in the longitudinal direction of the absorbent product certainly.

In the absorbent product, preferably, the other side wall end part out of the two side wall end parts comprises: a half standing part being continuous from the standing part and not being bonded to the bonded part nor the main body part, the elastic members being arranged on the half standing part, the half standing part standing up from the main body part by contraction of the elastic members lower than the standing part; and a bonded section which is provided adjacent to the outside of the half standing part and is bonded on the bonded part.

Preferably, the absorbent product is an absorbent pad for light incontinence, which is attached on an inner side of an exterior product worn by a wearer.

These and other objects, features, aspects and advantages of the present invention will become more apparent from the following detailed description of the present invention when taken in conjunction with the accompanying drawings.

DESCRIPTION OF THE INVENTION

Figure 1:
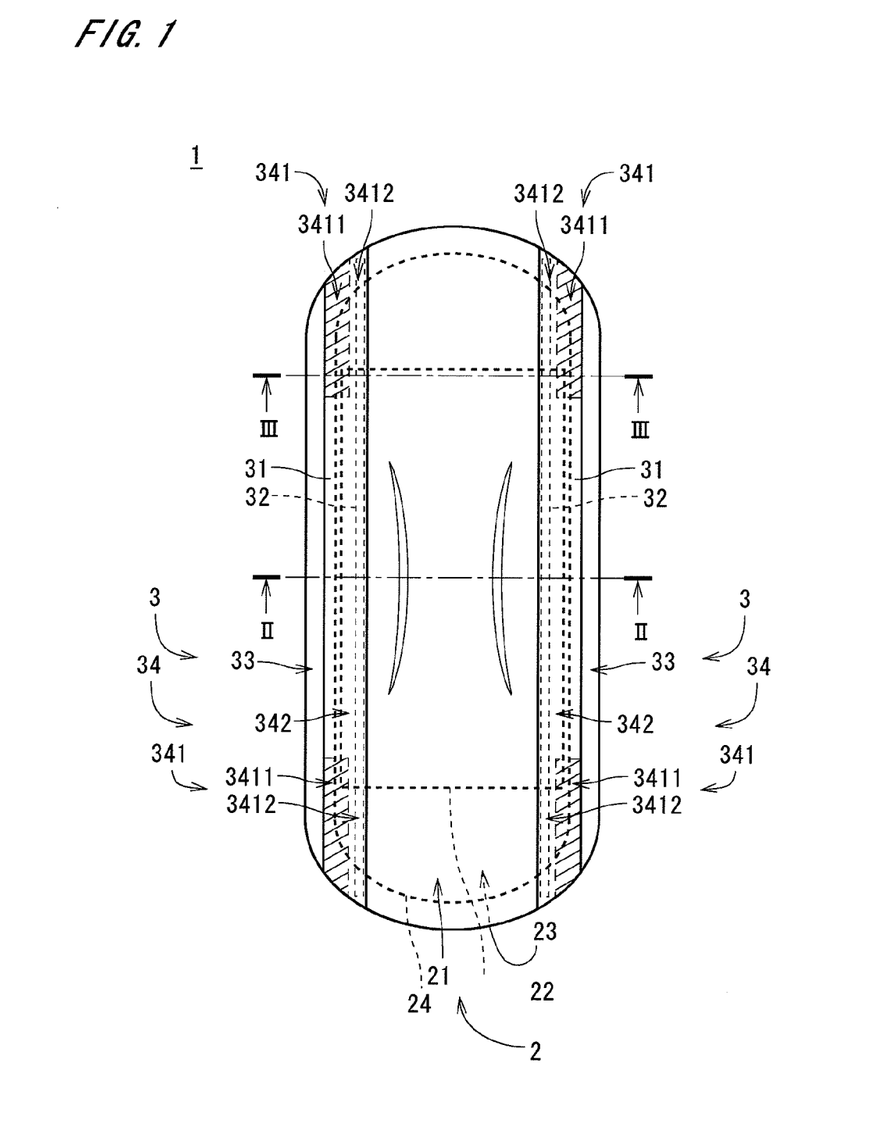
FIG. 1 is a plan view of an absorbent product in accordance with the first preferred embodiment.

FIG. 1 is a plan view showing an absorbent product 1 in accordance with the first preferred embodiment of the present invention. The absorbent product 1 is an absorbent pad for light incontinence attached on an inner side of underpants which is an exterior product worn by the wearer in order to receive excrement such as urine discharged from the wearer (i.e., the inner side is a side which comes into contact with the wearer). The absorbent product 1 is an absorbent pad whose amount of absorption indicated by its package or the like is about equal to or smaller than 200 ml (milliliter), and the amount of absorption in the present preferred embodiment is equal to or larger than 20 ml and equal to or smaller than 40 ml. The actual amount of absorption of the absorbent product 1 is larger than the one indicated by the package. FIG. 1 shows a surface of the absorbent product 1, which is to come into contact with the wearer's body during use (the surface is hereinafter referred to as an "upper surface").

Figure 2:
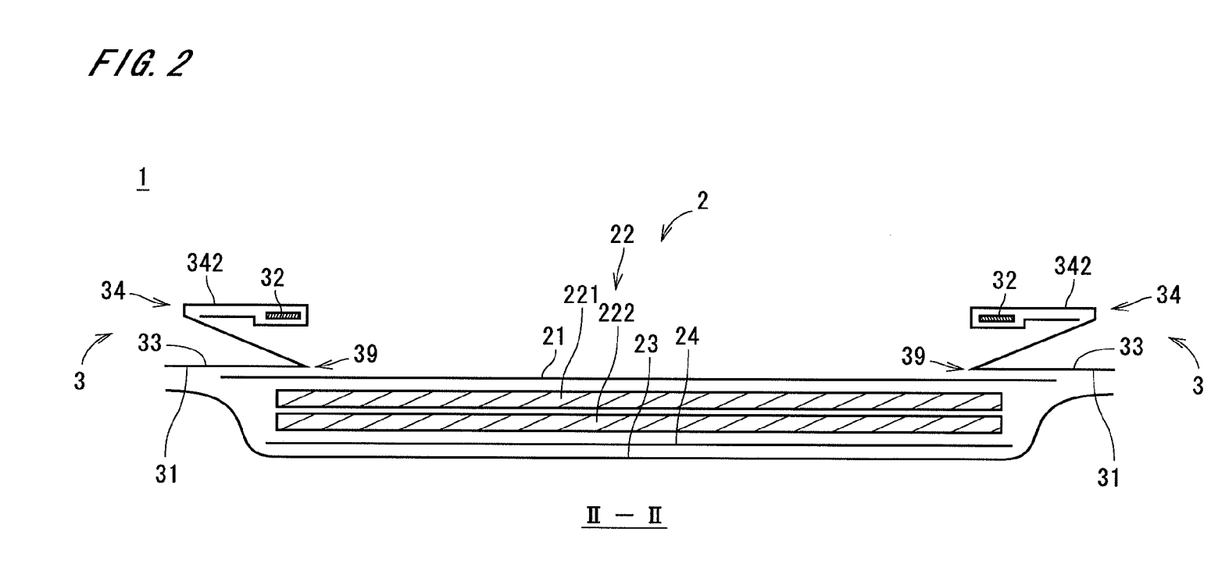
FIGS. 2 and 3 are cross-sectional views of the absorbent product.
Figure 3:
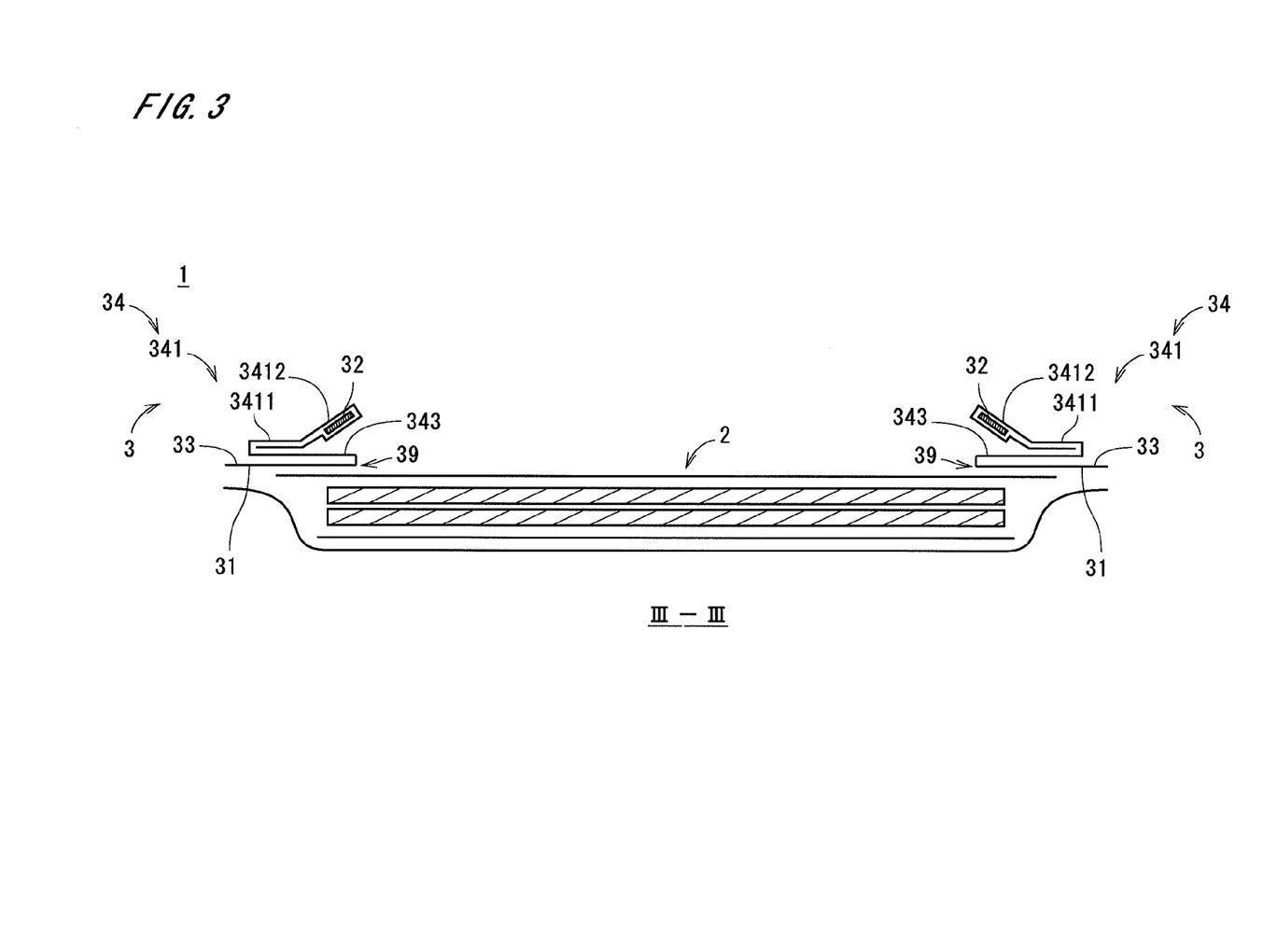

FIG. 2 is a cross-sectional view of the absorbent product 1 taken along a plane perpendicular to a longitudinal direction (i.e., a vertical direction in FIG. 1) of the absorbent product 1 at the positions indicated by the arrows II-II shown in FIG. 1. FIG. 3 is a cross-sectional view of a portion of the absorbent product 1, which is near to its upper end portion in FIG. 1, taken along a plane perpendicular to the longitudinal direction at the positions indicated by the arrows III-III. The cross section of a portion which is near to a lower end portion of the absorbent product 1 in FIG. 1 is the same as that shown in FIG. 3.

As shown in FIGS. 1 and 2, the absorbent product 1 has a sheet-like main body part 2 in which a back sheet 23, a deodorant sheet 24, an absorbent core 22, and a top sheet 21 are laminated in this order from a lower side (i.e., from a side opposed to the side coming into contact with the wearer) and a pair of side sheets 3 which are located on both side portions of the main body part 2 (i.e., on both sides in a width direction perpendicular to the longitudinal direction), over the almost entire length in the longitudinal direction of the main body part 2. In the main body part 2, the top sheet 21 covers an upper surface of the absorbent core 22 which is an absorbent positioned between the top sheet 21 and the back sheet 23, and the back sheet 23 covers a lower surface of the absorbent core 22 (i.e., the upper surface is one main surface of the absorbent core 22, which comes into contact with the wearer, and the lower surface is the other main surface opposed to the one main surface). The top sheet 21 and the back sheet 23 are bonded to each other around the absorbent core 22 and the deodorant sheet 24 by using hot melt adhesive or the like. In FIG. 2, respective constituent elements of the main body part 2 and the side sheets 3 are shown separately for convenience of illustration (the same is applied in FIG. 3).

The top sheet 21 is a nonwoven fabric made of liquid-pervious sheet material, for example, hydrophilic fiber, and the top sheet 21 immediately catches moisture of excrement from the wearer and moves the moisture into the absorbent core 22. Examples of the nonwoven fabric used for the top sheet 21 are a point-bond nonwoven fabric, air-through nonwoven fabric, or spunlace nonwoven fabric, and normal hydrophilic fibers for making these nonwoven fabrics are cellulose, rayon, cotton or the like. As the top sheet 21, a liquid-pervious nonwoven fabric made of hydrophobic fiber (for example, polypropylene, polyethylene, polyester, polyamide, or nylon) with hydrophilic treatment using a surfactant may be utilized or a microporous plastic film may be used.

The absorbent core 22 has two layers of core members 221, 222 (see FIG. 2) which are laminated in a thickness direction. Each of the core members 221, 222 has a structure in which granulated high absorbent polymers (e.g., SAP (Super Absorbent Polymer)) are fixed between two nonwoven fabrics with use of hot melt adhesive or the like, and the two nonwoven fabrics are bonded by hot melt adhesive, heat sealing, or the like. The absorbent core 22 rapidly absorbs and retains moisture which has passed through the top sheet 21. In each core member, the high absorbent polymers are fixed on a plurality of areas each of which continuously extends in the longitudinal direction in strip form, forming an array in the width direction. The two nonwoven fabrics are bonded on clearances between the plurality of areas by using heat sealing or the like (i.e., the clearances are areas in which no high absorbent polymers exist), and each of the plurality of areas in which the high absorbent polymers exist are thereby sealed.

The structure of the core members 221, 222 is not limited to the above-described one, but may be a structure where a mixture of hydrophilic fibers (e.g., crushed pulp fibers or cellulose fibers) and the granulated high absorbent polymers is wrapped by a cover sheet such as a tissue paper or a liquid-pervious nonwoven fabric. In this case, the cover sheet is bonded to the hydrophilic fibers and the high absorbent polymers with the hot melt adhesive, to prevent deformation of the hydrophilic fibers and falling of the high absorbent polymers (especially, falling after absorption of moisture). The absorbent core 22 may be formed by one core member.

The back sheet 23 is a water-repellent or liquid-impervious plastic film, and the back sheet 23 prevents the excrement which has passed through the top sheet 21 from leaking outside the main body part 2. From the view point of preventing sweatiness of the absorbent product 1 and providing comfortable feeling to the wearer, it is preferable that a plastic film with permeability (i.e., breathability) is used as the back sheet 23. As the back sheet 23, a water-repellent or liquid-impervious nonwoven fabric (e.g., a spunbond nonwoven fabric, a meltblown nonwoven fabric, or a SMS (spunbond-meltblown-spunbond) nonwoven fabric) or a laminated sheet where a water-repellent or liquid-impervious plastic film is laminated on the water-repellent or liquid-impervious nonwoven fabric can be used.

The deodorant sheet 24 is a hydrophilic sheet member including deodorant agent and for example, cellulose or pulp is used as hydrophilic fibers forming the deodorant sheet 24. As the deodorant agent, inorganic porous crystal such as zeolite which preferably supports metal (e.g., silver, copper, zinc, iron, nickel cobalt, palladium, platinum) is used preferably.

Each of the pair of side sheets 3 is formed by bonding elastic members 32 extending in the longitudinal direction, to a side sheet main body 31 which is a water-repellent or liquid-impervious sheet member, as shown in FIGS. 1 to 3. The side sheet main body 31 is formed by, e.g., a spunbond nonwoven fabric, a meltblown nonwoven fabric, a SMS nonwoven fabric, or an air-through nonwoven fabric. The side sheet main body 31 may be formed by a plastic film or a laminated sheet of the above nonwoven fabric and the plastic film. Since a plastic film with permeability is used in this case, it is possible to prevent sweatiness of the absorbent product 1 and to provide comfortable feeling to the wearer. The elastic members 32 are strip-like polyurethane films and bonded on the side sheet main body 31 by the hot melt adhesive. Other examples of the elastic members 32 include strip-like natural rubbers, polyurethane yarns which are elastic yarns, yarn-like natural rubbers, or the like.

As shown in FIGS. 1 to 3, each of the pair of side sheets 3 extending in the longitudinal direction has a strip-like bonded part 33 which is one side of a fold line 39 of the side sheet 3 (see FIGS. 2 and 3) and a side wall part 34 which is the other side of the fold line 39, the fold line 39 being provided over the entire length of the side sheet 3. The bonded part 33 is bonded on the main body part 2 (i.e., on the side coming into contact with the wearer) over the entire length of the side sheet 3, in the vicinity of a side edge of the main body part 2, by using the hot melt adhesive. As shown in FIGS. 2 and 3, the side wall part 34 is folded toward the outside in the width direction at the fold line 39 (i.e., an inner edge of the bonded part 33, which is located in the inside in the width direction), and further folded inwardly at a position apart from the fold line 39, and a part of the side wall part 34 (a standing part 342 (see FIG. 2) and a half standing part 3412 (see FIG. 3) discussed later) stands up from the main body part 2. In other words, the side sheet 3 is folded outwardly at the fold line 39, and the side wall part 34 which is a portion folded outwardly in the side sheet 3 is folded inwardly at the almost center in the width direction (i.e., at a position away from the fold line 39) and toward the side coming into contact with the wearer.

Each side wall part 34 has two side wall end parts 341 which are overlaid and bonded on the both end portions of the strip-like bonded part 33 by heat sealing, and each side wall end part 341 is fixed on the main body part 2 with interposing the bonded part 33, as shown in FIGS. 1 and 3. The side wall part 34 has a standing part 342 being continuous from the two side wall end parts 341 between the two side wall end parts 341 and standing up from the main body part 2, as shown in FIGS. 1 and 2.

As shown in FIGS. 1 and 3, each of the two side wall end parts 341 has a bonded section 3411 fixed on the bonded part 33 by heat sealing (i.e., fixed on the main body part 2 indirectly with interposing the bonded part 33) and a half standing part 3412 being continuous from the standing part 342 and being adjacent to the bonded section 3411 on the inside in the width direction. The strip-like half standing part 3412 extending in the longitudinal direction is not bonded to the bonded part 33 nor the main body part 2, and the half standing part 3412 stands up from the main body part 2 lower than the standing part 342 (i.e., lower than an uppermost portion of the standing part 342). As shown in FIG. 1, the half standing part 3412 is continuous from the standing part 342 to an end (i.e., an edge) in the longitudinal direction of the side sheet 3, and is overlaid with an end in the longitudinal direction of the absorbent core 22. In FIG. 1, each bonded section 3411 of the pair of side wall parts 34 is hatched for easy understanding of illustration (the same is applied in FIGS. 4, 5, 7, 8, and 9).

As shown in FIGS. 1 to 3, the side wall part 34 has strip-like elastic members 32 arranged over almost entire length in the longitudinal direction of the side wall part 34 (i.e., arranged over the entire length in the longitudinal direction of the standing part 342 and almost entire length of the two half standing parts 3412). When the absorbent product 1 is worn by the wearer, the extended elastic members 32 which are bonded on both of the standing part 342 and the two half standing parts 3412 in each side sheet 3 contract the standing part 342 in the longitudinal direction to form gathers, and the standing part 342 stands up from the fold line 39 located at an inner position than the side edge of the main body part 2 (i.e., at a position on the main body part 2, which is an inner position than the side edge of the main body part 2). The two half standing parts 3412 contract in the longitudinal direction and stand up from inner edges of the bonded sections 3411. Then, the standing parts 342 and the half standing parts 3412 fit the vicinity of wearer's crotch in wearing.

In the absorbent product 1, since the side wall end parts 341 are provided with the half standing parts 3412 in the vicinity of end portions in the longitudinal direction of the pair of side wall parts 34, it is possible to prevent moisture such as urine which has reached the side wall end parts 341 from leaking out to the sides of the absorbent product 1 beyond the side wall parts 34. In other words, it is possible to prevent side leakage from the vicinity of end portions in the longitudinal direction of the absorbent product 1. In the absorbent product 1, sufficiently securing the length of the bonded section 3411 which is provided adjacent to the outside of the half standing part 3412 in each side wall end part 341, makes it possible to surely joint the side wall end part 341 and the bonded part 33 to thereby keep the form of gathers formed by the standing parts 342 and the half standing parts 3412 properly.

In each side sheet 3, since the side wall part 34 is folded outwardly at the fold line 39 and further folded inwardly at a position away from the fold line 39, the half standing part 3412 and a portion 343 facing the half standing part 3412 (the portion 343 is hereinafter referred to as a "facing part 343") is not bonded to the bonded part 33 nor the main body part 2 in the side wall end part 341. As a result, it is possible to largely stand up the half standing part 3412 from the main body part 2, thereby surely preventing side leakage from the vicinity of end portions in the longitudinal direction of the absorbent product 1. Since each side wall end part 341 has a structure in which the water-repellent or liquid-impervious half standing part 3412 and the water-repellent or liquid-impervious facing part 343 face each other, moisture which has reached the side wall end part 341 from the standing part 342 can be flown back to the main body part 2 by both of the half standing part 3412 and the facing part 343 rapidly. Consequently, it is possible to surely prevent side leakage from the vicinity of end portions in the longitudinal direction of the absorbent product 1.

The above structure of the absorbent product 1 is especially suitable for a small absorbent pad for light incontinence, which has relatively high necessity of preventing side leakage from the vicinity of end portions in the longitudinal direction, because the longitudinal length of the absorbent product 1 is short and there is a relatively high possibility that moisture such as urine reaches the end portions in the longitudinal direction before it is absorbed into the absorbent core.

In the absorbent product 1, since each of the two side wall end parts 341 of each side wall 34 has the half standing part 3412 and the bonded section 3411, it is possible to prevent side leakage from the vicinity of both end portions in the longitudinal direction of the absorbent product 1. The form of gathers formed by the standing parts 342 and the half standing parts 3412 can be kept properly.

In each side wall part 34, the half standing part 3412 is continuous from the standing part 342 to the end of the side sheet 3 as discussed above. Sufficiently securing the length of the half standing part 3412 makes it possible to surely prevent side leakage from the vicinity of end portions in the longitudinal direction of the absorbent product 1.

Since the half standing part 3412 is overlaid with the end in the longitudinal direction of the absorbent core 22 (i.e., an end of the half standing part 3412 opposed to the standing part 342 is located between the end of the absorbent core 22 and the end of the main body part 2 or overlaid with the end of the absorbent core 22), the moisture which has flown back to the main body part 2 from the half standing part 3412 of the side wall end part 341 can be absorbed into the absorbent core 22 rapidly. As a result, it is possible to surely prevent side leakage from the vicinity of end portions in the longitudinal direction of the absorbent product 1.

Figure 4:
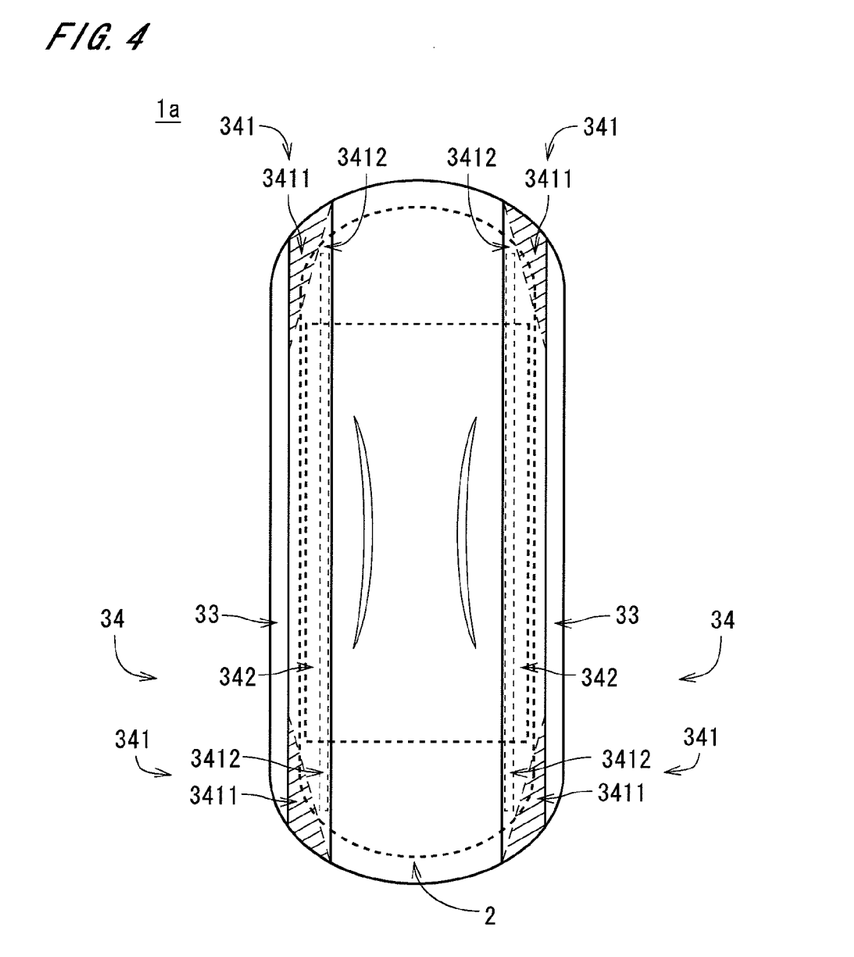
FIG. 4 is a plan view of an absorbent product in accordance with the second preferred embodiment.

Next discussion will be made on an absorbent product in accordance with the second preferred embodiment of the present invention. FIG. 4 is a plan view showing an absorbent product 1*a* according to the second preferred embodiment. In the absorbent product 1*a*, the forms of the bonded sections 3411 and the half standing parts 3412 in the two side wall end parts 341 of each side wall part 34 are different from those shown in FIG. 1. The other constituent elements are the same as those in the absorbent product 1 shown in FIGS. 1 to 3 and represented by the same reference signs.

As shown in FIG. 4, the width of the half standing part 3412 in the width direction gradually decreases as being away from the standing part 342 in the absorbent product 1*a* which is spread in the longitudinal direction. In other words, the border between the half standing part 3412 and the bonded section 3411 directs toward the inside as being away from the standing part 342. The end of the side wall end part 341 (i.e., the end opposed to the standing part 342) in the longitudinal direction is bonded to the bonded part 33 over the entire width thereof.

Similarly to the first preferred embodiment, since the side wall end part 341 is provided with the half standing part 3412 in the side wall part 34 which is folded into two on the bonded part 33, it is possible to prevent side leakage from the vicinity of end portions in the longitudinal direction of the absorbent product 1*a*. Sufficiently securing the length of the bonded section 3411 in each side wall end part 341 makes it possible to surely join the side wall end part 341 and the bonded part 33 and to keep the form of gathers formed by the standing parts 342 and the half standing parts 3412 properly.

In the absorbent product 1*a* according to the second preferred embodiment, since the width of the half standing part 3412 in the width direction gradually decreases as being away from the standing part 342, moisture which has reached the side wall end part 341 from the standing part 342 can be directed toward the inside along the border between the half standing part 3412 and the bonded section 3411 rapidly, to be flown back to the main body part 2 quickly. As a result, it is possible to prevent side leakage from the vicinity of end portions in the longitudinal direction of the absorbent product 1*a* certainly. Since the end of the side wall end part 341 in the longitudinal direction is bonded to the bonded part 33 over the entire width thereof, moisture which has reached the side wall end part 341 can be flown back to the main body part 2 more reliably. Thus, it is possible to surely prevent side leakage from the vicinity of end portions in the longitudinal direction of the absorbent product 1*a*.

Figure 5:
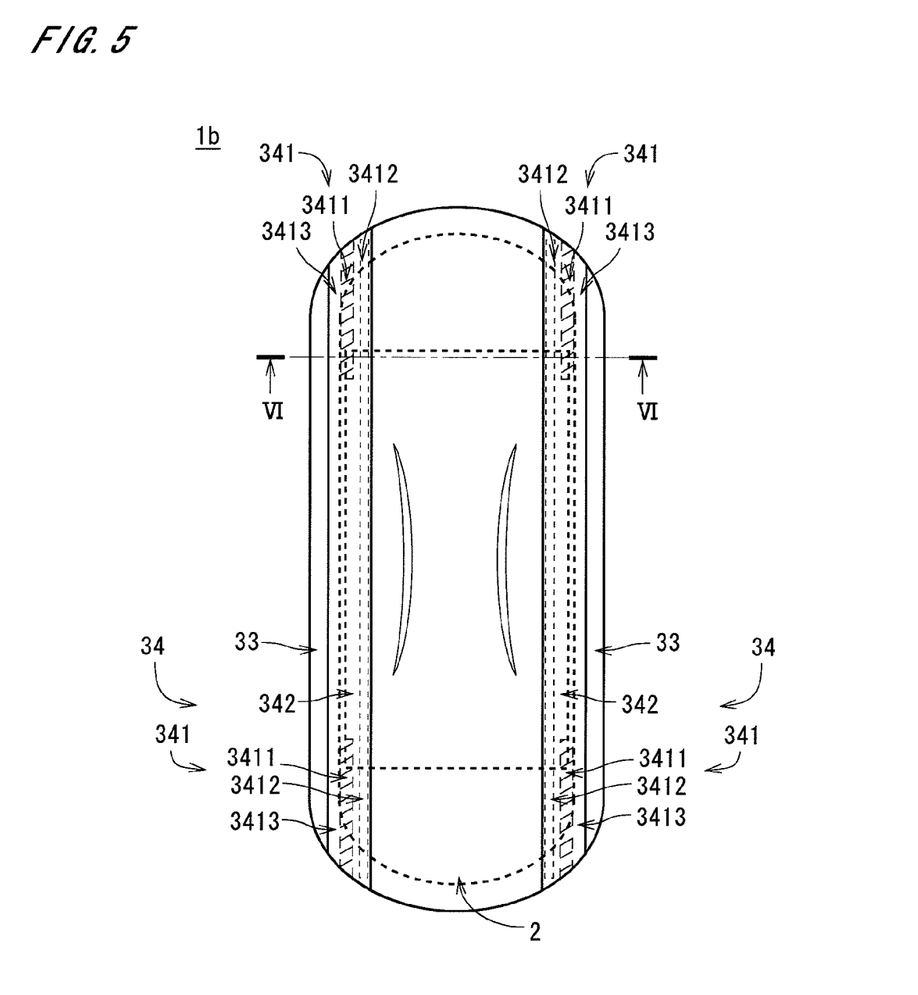
FIG. 5 is a plan view of an absorbent product in accordance with the third preferred embodiment.
Figure 6:
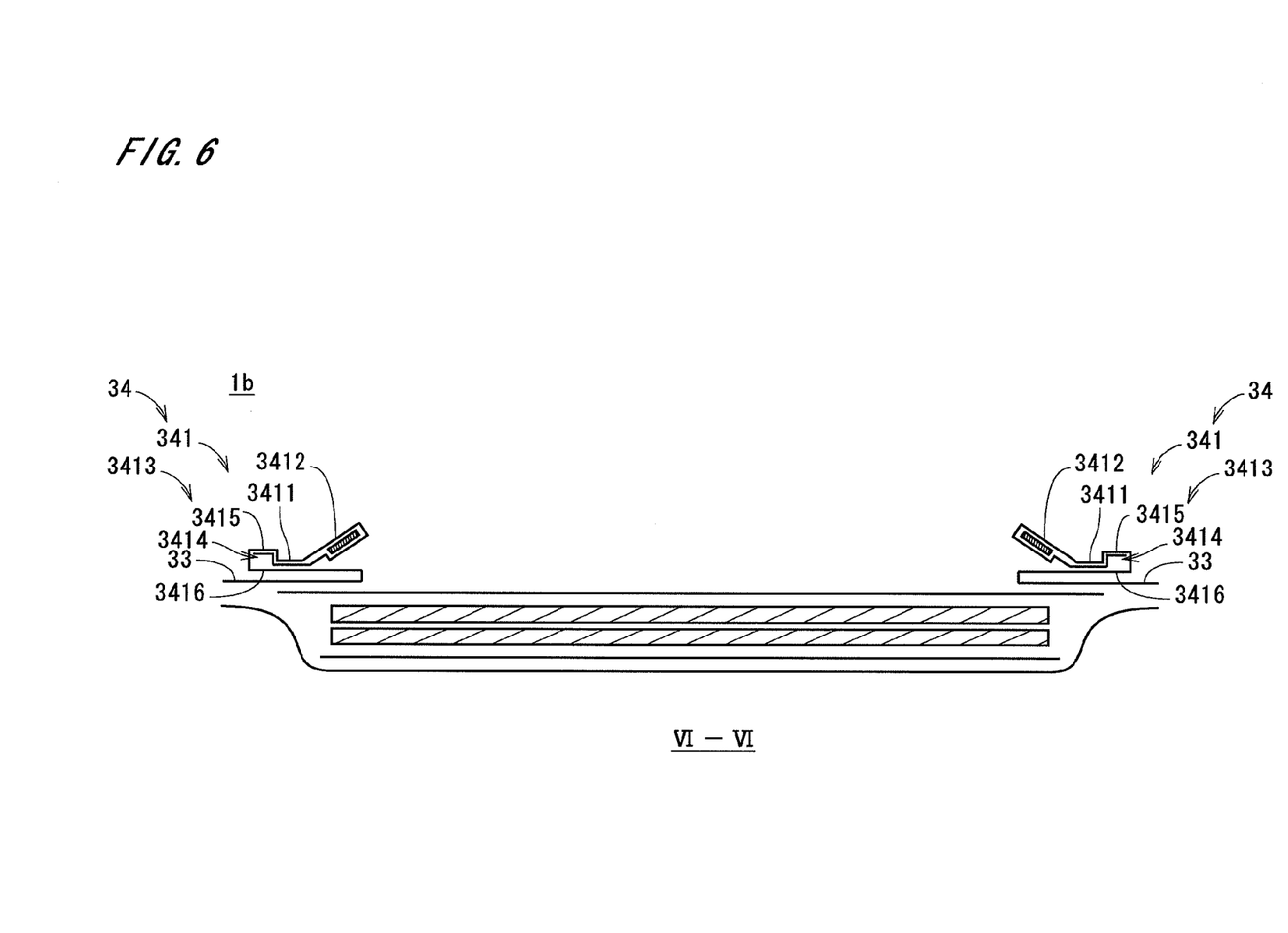
FIG. 6 is a cross-sectional view of the absorbent product.

Next discussion will be made on an absorbent product in accordance with the third preferred embodiment of the present invention. FIG. 5 is a plan view showing an absorbent product 1*b* according to the third preferred embodiment. FIG. 6 is a cross-sectional view of the absorbent product 1*b* taken along a plane perpendicular to the longitudinal direction (i.e., a vertical direction in FIG. 5) of the absorbent product 1*b* at the positions indicated by the arrows VI-VI shown in FIG. 5, and corresponds to FIG. 3 discussed above. In the absorbent product 1*b*, the structure of the two side wall end parts 341 of each side wall part 34 is different from that shown in FIG. 1. The other constituent elements are the same as those in the absorbent product 1 shown in FIGS. 1 to 3 and represented by the same reference signs.

As shown in FIGS. 5 and 6, the bonded section 3411 is located outside the half standing part 3412 in each side wall end part 341 in the absorbent product 1*b* similarly to the first preferred embodiment, and the form of the half standing part 3412 is the same as that in the first preferred embodiment. Differently from the first preferred embodiment, each side wall end part 341 further has a tubular space forming part 3413 which is located adjacent to the outside of the bonded section 3411 and is not bonded to the bonded part 33 nor the main body part 2, extending in the longitudinal direction above the bonded part 33 in the absorbent product 1*b*. In other words, the bonded section 3411 is sandwiched between the half standing part 3412 and the tubular space forming part 3413 in the width direction. As shown in FIG. 5, the tubular space forming part 3413 is a portion which is continuous from the standing part 342 similarly to the half standing part 3412.

In the tubular space forming part 3413, the side wall part 34 is folded tubularly and laminated as an upper layer 3415 and a lower layer 3416 (in detail, the upper layer 3415 consists of two layers of nonwoven fabrics bonded each other), as shown in FIG. 6. The upper layer 3415 and the lower layer 3416 are not bonded each other to thereby provide a tubular space 3414 between the upper layer 3415 and the lower layer 3416. In FIG. 6, the tubular space 3414 is drawn higher than actual, and illustrated as a rectangle for easy understanding of illustration.

The tubular space 3414 is continuous with a space sandwiched in the width direction between the pair of standing parts 342 on the main body part 2 shown in FIG. 2 (i.e., the space is an inner space sandwiched by the pair of standing parts 342). Therefore, the moisture which has reached the side wall end part 341 from the standing part 342 (see FIG. 5) (especially, the moisture which has moved an outer portion of the standing part 342) is temporally retained in the tubular space 3414, and it is flown back to the main body part 2 through the standing part 342 in the absorbent product 1*b*. As a result, it is possible to surely prevent side leakage from the vicinity of end portions in the longitudinal direction of the absorbent product 1*b*, even if relatively large amount of moisture has reached the side wall end parts 341.

Figure 7:
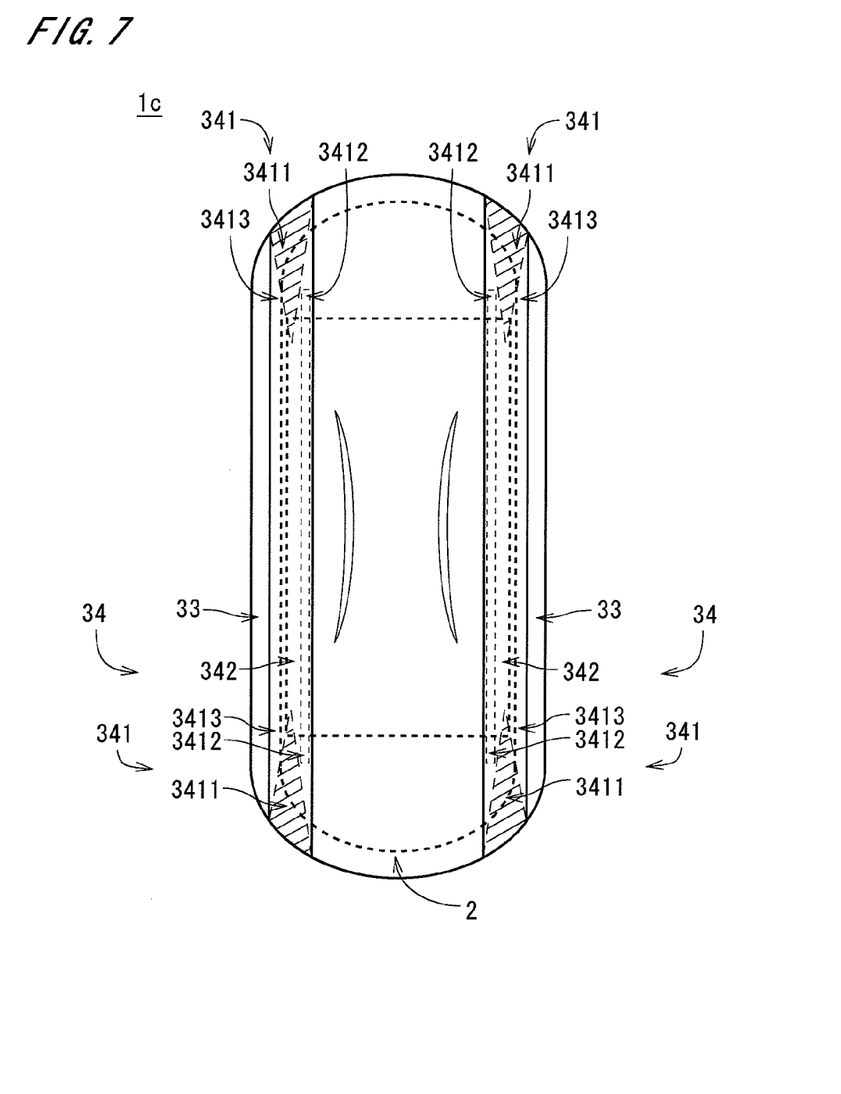
FIG. 7 is a plan view of an absorbent product in accordance with the fourth preferred embodiment.

Next, discussion will be made on an absorbent product in accordance with the fourth preferred embodiment of the present invention. FIG. 7 is a plan view showing an absorbent product 1*c* according to the fourth preferred embodiment. In the absorbent product 1*c*, the forms of the bonded sections 3411, the half standing parts 3412, and the tubular space forming parts 3413 in the two side wall end parts 341 of each side wall part 34 are different from those shown in FIG. 5. The other constituent elements are the same as those in the absorbent product 1b shown in FIGS. 5 and 6 and represented by the same reference signs.

As shown in FIG. 7, the width of the half standing part 3412 in the width direction gradually decreases as being away from the standing part 342 in the absorbent product 1c which is expanded in the longitudinal direction, similarly to the second preferred embodiment. In the absorbent product 1c, the width of the tubular space forming part 3413 in the width direction gradually decreases as being away from the standing part 342. In other words, the border between the tubular space forming part 3413 and the bonded section 3411 extends toward the inside as being near to the standing part 342. The end in the longitudinal direction of the side wall end part 341 (i.e., the end opposed to the standing part 342) is bonded to the bonded part 33 over the entire width thereof.

Similarly to the third preferred embodiment, since the moisture which has reached the side wall end part 341 from the standing part 342 is temporally retained in the tubular space 3414 (see FIG. 6) provided in the tubular space forming part 3413 and thereafter it is flown back to the main body part 2 through the standing part 342 in the absorbent product 1c, it is possible to surely prevent side leakage from the vicinity of end portions in the longitudinal direction of the absorbent product 1c. Since the width of the tubular space forming part 3413 gradually decreases as being away from the standing part 342, the moisture which has been temporarily retained in the tubular space 3414 can be directed toward the inside along the border between the tubular space forming part 3413 and the bonded section 3411 rapidly, to be flown back to the main body part 2 quickly. Consequently, it is possible to prevent side leakage from the vicinity of end portions in the longitudinal direction of the absorbent product 1c certainly. Further, since the end in the longitudinal direction of the side wall end part 341 is bonded to the bonded part 33 over the entire width thereof, the moisture which has been temporarily retained in the tubular space 3414 can be flown back to the main body part 2 more reliably. Thus, it is possible to surely prevent side leakage from the vicinity of end portions in the longitudinal direction of the absorbent product 1c.

Figure 8:
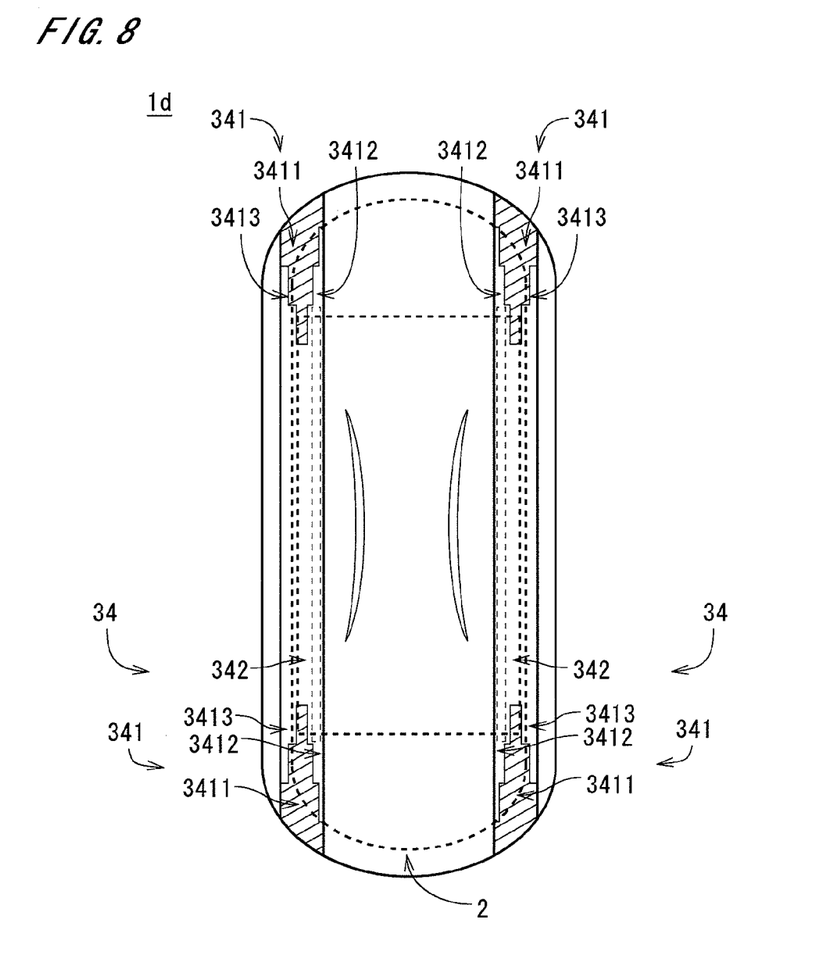
FIG. 8 is a plan view of an absorbent product in accordance with the fifth preferred embodiment.

Next, discussion will be made on an absorbent product in accordance with the fifth preferred embodiment of the present invention. FIG. 8 is a plan view showing an absorbent product 1d according to the fifth preferred embodiment. In the absorbent product 1d, the forms of the bonded sections 3411, the half standing parts 3412, and the tubular space forming parts 3413 in the two side wall end parts 341 of each side wall part 34 are different from those shown in FIG. 7. The other constituent elements are the same as those in the absorbent product 1c shown in FIG. 7 and represented by the same reference signs. In FIG. 8, the shape of the bonded sections 3411 is drawn by a solid line for easy understanding of illustration.

As shown in FIG. 8, the width of the half standing part 3412 and the tubular space forming part 3413 in the width direction gradually decreases as being away from the standing part 342 in the absorbent product 1d which is expanded in the longitudinal direction, similarly to the fourth preferred embodiment. In the absorbent product 1d, the bonded section 3411 formed between the half standing part 3412 and the tubular space forming part 3413 is a group of a plurality of approximately rectangular areas arranged in the longitudinal direction, and the width of the areas increases as being away from the standing part 342 in stages. Therefore, the width of the half standing part 3412 and the tubular space forming part 3413 decreases as being away from the standing part 342 in stages.

Similarly to the fourth preferred embodiment, it is possible to surely prevent side leakage from the vicinity of end portions in the longitudinal direction of the absorbent product 1d by the tubular space 3414 (see FIG. 6) provided in the tubular space forming part 3413 in the absorbent product 1d. The form of the bonded section 3411 is simplified in the absorbent product 1d to make the manufacturing process of the absorbent product 1d easier.

Though the preferred embodiments of the present invention have been discussed above, the present invention is not limited to the above-discussed preferred embodiments, but allows various variations.

Figure 9:
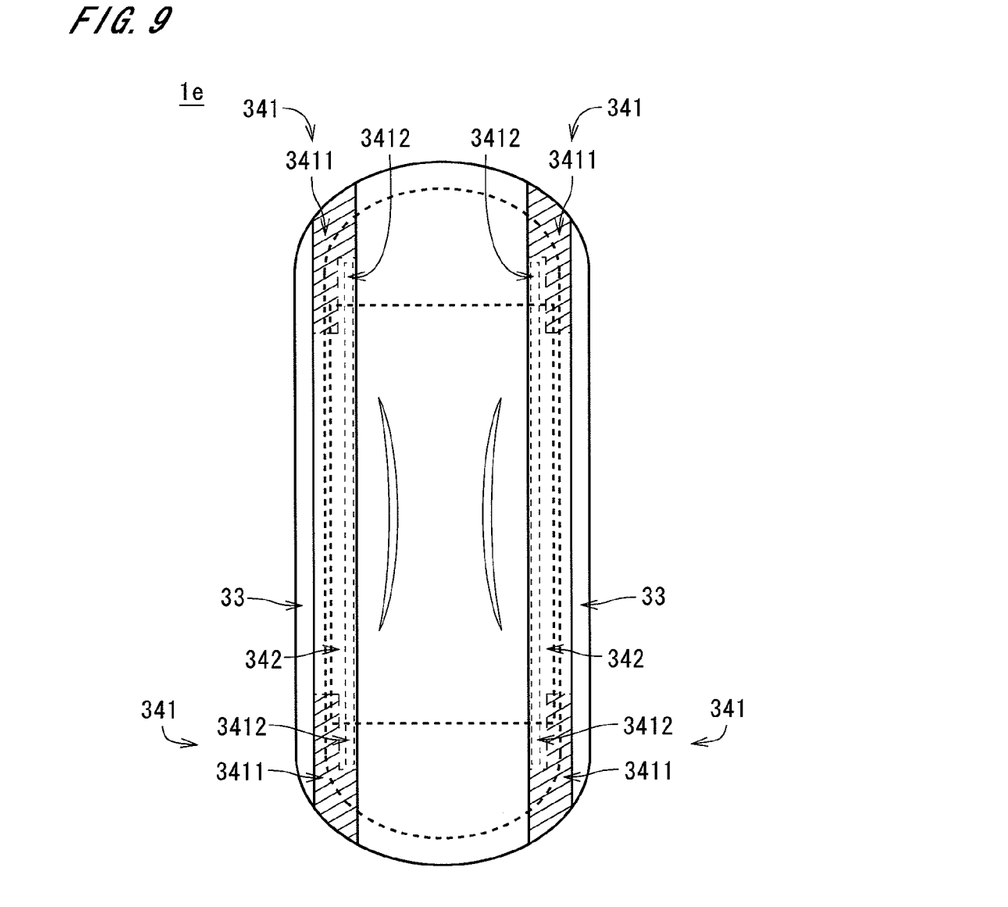
FIG. 9 is a plan view showing another example of the absorbent product.

The forms of the bonded section 3411 and the half standing part 3412 in the side wall end part 341 is not limited to those shown in FIGS. 1, 4, 5, 7 and 8, but for example, there may be a case where the half standing part 3412 having a rectangular shape is provided from the standing part 342 to the almost center in the longitudinal direction of the side wall end part 341, and a portion from the almost center to the end in the longitudinal direction of the side wall end part 341 is fixed on the bonded part 33 over the entire width, like an absorbent product 1e shown in FIG. 9. That is, in the side wall end part 341, a portion which is adjacent to the outside of the half standing part 3412 and a portion which is closer to the end of the side wall end part 341 than the half standing part 3412 function as the bonded section 3411.

The bonded section 3411 may be fixed on the bonded part 33 by ultrasonic bonding, the hot melt adhesive, a combination of heat sealing and the hot melt adhesive, or the like. In a case where the form of the bonded section 3411 is complicated like in the absorbent product 1a shown in FIG. 4 and the absorbent products 1c to 1e shown in FIGS. 7 to 9, it is preferable to use the heat sealing which can be applied to the bonding of the bonded section 3411 having a complicated form.

In a case where the necessity of preventing side leakage from one side wall end part 341 out of the two side wall end parts 341 in each side wall part 34 is larger than that of the other side wall end part 341 or the like in the above absorbent products 1, 1a to 1e, there may be a case where only one side wall end part 341 is provided with the half standing part 3412, and the whole of the other side wall end part 341 is bonded on the bonded part 33 (i.e., the whole of the other side wall end part 341 may be the bonded section 3411). Even in this case, it is possible to prevent side leakage from the vicinity of one end portion in the longitudinal direction of the absorbent product. As discussed above, when the half standing part 3412 is only provided in one side wall end part 341 in each side wall part 34, the elastic members 32 are provided from the half standing part 3412 of the one side wall end part 341 up to the standing part 342, and one end of the elastic members 32 is located on the above half standing part 3412. The other end of the elastic members 32 is not necessarily located on the border between the standing part 342 and the other side wall end part 341, but may be located slightly away from the border on the standing part 342. In other words, in the standing part 342, the elastic members 32 may be arranged over the almost entire length in the longitudinal direction of the standing part 342.

The above-discussed structures of the absorbent products may be applied to various absorbent products such as a disposal diaper, an auxiliary absorbent pad which is attached on an inner side of a disposal diaper, a sanitary napkin, and a panty liner, as well as a light incontinence pad.

While the invention has been shown and described in detail, the foregoing description is in all aspects illustrative and not restrictive. It is therefore understood that numerous modifications and variations can be devised without departing from the scope of the invention.

This application claims priority benefit under 35 U.S.C. Section 119 of Japanese Patent Application No. 2008-268097 filed in the Japan Patent Office on Oct. 17, 2008, the entire disclosure of which is incorporated herein by reference.

What is claimed is:

1. An absorbent product for receiving excrement from a wearer, the absorbent product comprising:
   a sheet-like main body part including an absorbent core positioned between a back sheet and a top sheet; and
   a pair of side sheets located on two side portions of said main body part, respectively, said side sheets extending in a longitudinal direction of said main body part,
   wherein each of said side sheets comprises:
   (i) a fold line extending over an entire length of said side sheet;
   (ii) a strip-like bonded part bonded on said main body part, the strip-like bonded part being disposed on one side of said fold line, and an inner edge of said strip-like bonded part being said fold line; and
   (iii) a side wall part which is disposed on an opposite side of the fold line from the strip-like bonded part, the side wall part having a first portion folded outwardly in a width direction perpendicular to the longitudinal direction at said fold line and a second portion folded inwardly in said width direction at a position apart from said fold line, wherein a part of said side wall part stands up from said main body part,
   wherein said side wall part is water-repellent or liquid-impervious,
   wherein said side wall part of each of the side sheets comprises:
   (i) two side wall end parts which are bonded, respectively, on two end portions of said strip-like bonded part;
   (ii) a standing part being continuous from said two side wall end parts between said two side wall end parts and standing up from said fold line; and
   (iii) elastic members arranged over almost an entire length in said longitudinal direction of said standing part, the elastic members contracting said standing part to form gathers, and
   wherein one side wall end part out of said two side wall end parts comprises:
   (i) a half standing part formed by an inner part of said second portion of said side wall part and being continuous from said standing part and not being bonded to said bonded part nor said main body part, said elastic members being arranged on said half standing part, said half standing part standing up from said main body part by contraction of said elastic members to a height which is lower than a height of said standing part; and
   (ii) a bonded section which is provided on an outside of said half standing part in said width direction, the bonded section being bonded on said bonded part.

2. The absorbent product according to claim 1, wherein said half standing part is continuous from said standing part to an end of said side sheet.

3. The absorbent product according to claim 2, wherein said half standing part is overlaid with an end in said longitudinal direction of said absorbent core.

4. The absorbent product according to claim 3, wherein a width of said half standing part gradually decreases in a direction away from said standing part.

5. The absorbent product according to claim 4, wherein said one side wall end part further comprises a tubular space forming part which is continuous from said standing part and located adjacent to the outside of said bonded section and folded tubularly, to form a tubular space extending in said longitudinal direction.

6. The absorbent product according to claim 5, wherein the other side wall end part out of said two side wall end parts comprises:
   a half standing part being continuous from said standing part and not being bonded to said bonded part nor said main body part, said elastic members being arranged on said half standing part, said half standing part standing up from said main body part by contraction of said elastic members to a height which is lower than a height of said standing part; and
   a bonded section which is provided adjacent to an outside of said half standing part and is bonded on said bonded part.

7. The absorbent product according to claim 1, wherein said half standing part is overlaid with an end in said longitudinal direction of said absorbent core.

8. The absorbent product according to claim 7, wherein a width of said half standing part gradually decreases in a direction away from said standing part.

9. The absorbent product according to claim 8, wherein said one side wall end part further comprises a tubular space forming part which is continuous from said standing part and located adjacent to the outside of said bonded section and folded tubularly, to form a tubular space extending in said longitudinal direction.

10. The absorbent product according to claim 9, wherein the other side wall end part out of said two side wall end parts comprises:
    a half standing part being continuous from said standing part and not being bonded to said bonded part nor said main body part, said elastic members being arranged on said half standing part, said half standing part standing up from said main body part by contraction of said elastic members to a height which is lower than a height of said standing part; and
    a bonded section which is provided adjacent to an outside of said half standing part and is bonded on said bonded part.

11. The absorbent product according to claim 1, wherein a width of said half standing part gradually decreases in a direction away from said standing part.

12. The absorbent product according to claim 11, wherein said one side wall end part further comprises a tubular space forming part which is continuous from said standing part and located adjacent to the outside of said bonded section and folded tubularly, to form a tubular space extending in said longitudinal direction.

13. The absorbent product according to claim 12, wherein the other side wall end part out of said two side wall end parts comprises:
    a half standing part being continuous from said standing part and not being bonded to said bonded part nor said main body part, said elastic members being arranged on said half standing part, said half standing part standing up from said main body part by contraction of said elastic members to a height which is lower than of height of said standing part; and
    a bonded section which is provided adjacent to an outside of said half standing part and is bonded on said bonded part.

14. The absorbent product according to claim 1, wherein said one side wall end part further comprises a tubular space forming part which is continuous from said standing part and located adjacent to the outside of said bonded section and folded tubularly, to form a tubular space extending in said longitudinal direction.

15. The absorbent product according to claim 14, wherein the other side wall end part out of said two side wall end parts comprises:
- a half standing part being continuous from said standing part and not being bonded to said bonded part nor said main body part, said elastic members being arranged on said half standing part, said half standing part standing up from said main body part by contraction of said elastic members to a height which is lower than a height of said standing part; and
- a bonded section which is provided adjacent to an outside of said half standing part and is bonded on said bonded part.

16. The absorbent product according to claim 1, wherein the other side wall end part out of said two side wall end parts comprises:
- a half standing part being continuous from said standing part and not being bonded to said bonded part nor said main body part, said elastic members being arranged on said half standing part, said half standing part standing up from said main body part by contraction of said elastic members to a height which is lower than a height of said standing part; and
- a bonded section which is provided adjacent to an outside of said half standing part and is bonded on said bonded part.

17. The absorbent product according to claim 1, wherein said absorbent product is an absorbent pad for light incontinence, which is attached on an inner side of an exterior product worn by a wearer.

18. The absorbent product according to claim 1, wherein said half standing part extends inwardly in the width direction from said bonded section.

* * * * *